United States Patent [19]

Kämmerer et al.

[11] Patent Number: 4,636,513
[45] Date of Patent: Jan. 13, 1987

[54] ISOXAZOLE DERIVATIVES AND MEDICAMENTS CONTAINING THESE COMPOUNDS

[75] Inventors: Friedrich-Johannes Kämmerer, Hochheim am Main; Rudolf Schleyerbach, Hofheim am Taunus, both of Fed. Rep. of Germany

[73] Assignee: Hoechst Aktiengesellschaft, Fed. Rep. of Germany

[21] Appl. No.: 702,312

[22] Filed: Feb. 15, 1985

[30] Foreign Application Priority Data

Feb. 17, 1984 [DE] Fed. Rep. of Germany ....... 3405727

[51] Int. Cl.$^4$ .................. A61K 31/445; C07D 413/06
[52] U.S. Cl. ..................................... 514/326; 514/222; 514/234; 514/378; 546/209; 548/248; 544/60; 544/137
[58] Field of Search .................. 546/209; 544/60, 137; 548/248; 514/222, 234, 326, 378

[56] References Cited

U.S. PATENT DOCUMENTS 2,126,329 8/1938 Hoffer .................................. 546/209
2,212,767 8/1940 Blankart .............................. 546/209

Primary Examiner—Robert T. Bond
Attorney, Agent, or Firm—Finnegan, Henderson, Farabow, Garrett & Dunner

[57] ABSTRACT

4-Isoxazolecarboxylic acid amides of the general formula I

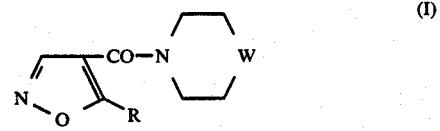

in which

R denotes hydrogen, alkyl with up to 4 carbon atoms or halogenoalkyl with up to 2 carbon atoms and W denotes a direct bond, $CH_2$, $CH-CH_3$, $CH-C_2H_5$, CHOH, O or S, processes for their preparation, medicaments which contain these compounds and the use of the compounds for the treatment of pain and/or fever.

9 Claims, No Drawings

ISOXAZOLE DERIVATIVES AND MEDICAMENTS CONTAINING THESE COMPOUNDS

The invention relates to novel 4-isoxazolecarboxylic acid amides of secondary cyclic amines, processes for their preparation and medicaments which contain these compounds and are particularly suitable for the treatment of pain and feverishness, and to the use of the compounds for the treatment of pain and feverishness.

The usual weak or mild analgesics which are used worldwide and are distinct from the powerful morphine-like analgesics, with their varying degree of ability to produce addiction and habituation, and are therefore frequently also designated "non-opioid" analgesics include the salicylates and pyrazolones and the aniline derivative Paracetamol (acetaminophen). The therapeutic experiences gained with these analgesics show that they are effective and exhibit an acceptable use/risk ratio. Nevertheless, it can be seen that there is no weak analgesic without side effects, sometimes of a very specific nature, of varying degrees of severity.

These include, for example, agranulocytosis following administration of pyrazolone, which, although it occurs extremely rarely, is sometimes fatal. Paracetamol is safe in the usual therapeutic doses, but is hepatotoxic if an overdose is taken. Gastrointestinal damage, such as occult hemorrhages in the mucous membrane, gastric ulcers and perforation of existing peptic ulcers, frequently occurs under acetylsalicylic acid medication; another disadvantage is the high rate of interaction with other medicaments.

There is therefore an urgent need for analgesics which do not have these undesirable side effects.

Surprisingly, it has now been found that the preparation of 4-isoxazolecarboxylic acid amides of secondary cyclic amines provides a class of compounds, the representatives of which have outstanding analgesic and antipyretic properties without gastric side effects, coupled with a good tolerance by the liver in chronic toxicity studies.

In contrast to most of the known weak analgesics, the compounds according to the invention remarkably display no antiflammatory action component. The reason for this is that the compounds according to the invention do not have an inhibiting influence on peripheral prostaglandin biosynthesis. This is at the same time the reason for their good gastric tolerance, since in the case of the analgesic antiflammatories, not only the therapeutically useful antiflammatory effect but also the undesirable gastrointestinal side effects are attributed precisely to this inhibition of prostaglandin synthetases in the peripheral tissue.

The novel 4-isoxazolecarboxylic acid amides are consequently antipyretic analgesics without an antiflammatory effect, which, from their effectiveness profile, are to be placed alongside the clinically established Paracetamol (cf. G. Kuschinsky and H. Lüllmann, Kurzes Lehrbuch der Pharmakologie [Short Textbook of Pharmacology], 6th revised and expanded edition, Georg Thieme Verlag Stuttgart 1974, page 109 et seq.).

A process for the preparation of isoxazolecarboxylic acid amides which have useful therapeutic properties and are therefore to be used as medicines is known from German Pat. No. 634,286. There are no indications of any activity in this patent. However, it has been found that the products obtained by the processes of Examples 5 and 6, which structurally are most comparable to the compounds according to the invention, have no analgesic action.

In German Pat. No. 653,835, which is a Patent of Addition to Pat. No. 634,286, the compounds of the main patent are attributed an analeptic action.

4-Isoxazole-carboxylic acid anilides with antiflammatory and analgesic properties are furthermore known from German Pat. No. 2,524,959. However, the antiflammatory action of these compounds is quite clearly predominant, and in this case also is largely to be attributed to inhibition of the peripheral prostaglandin biosynthesis.

In contrast, the invention relates to compounds of the formula (I) (see claim 1), in which R denotes hydrogen, alkyl with up to 4 carbon atoms or halogenoalkyl with up to 2 carbon atoms and W denotes a direct bond, $CH_2$, $CH—CH_3$, $CH—C_2H_5$, $CHOH$, O or S.

Preferred compounds are those in which R represents methyl, ethyl or trifluoromethyl. Of these compounds, those in which W represents $CH_2$ are in turn particularly preferred.

The invention also relates to processes for the preparation of compounds of the formula (I), wherein in the following description R and W have the abovementioned meanings. One process comprises reacting an amine of the formula II

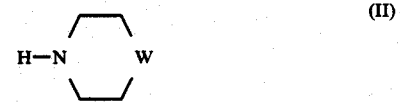

with a 4-isoxazolcarboxylic acid derivative of the formula III,

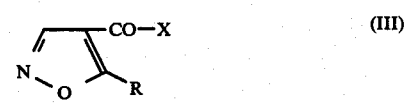

in which X is either a halogen atom or a YO— or ZO—CO—O— group, Y being unsubstituted phenyl or phenyl which contains one, two or three substituents selected from the group consisting of fluorine, chlorine, bromine, iodine, methyl, ethyl, methoxy, ethoxy, trifluoromethyl, the nitro group or cyano, or Y being an acyl group of the formula IIIa,

and Z being a substituent selected from the group consisting of alkyl having from 1 to 4 carbon atoms, phenyl or benzyl. If X is halogen, it is preferably chlorine or bromine.

The reaction is advantageously carried out in a distributing agent or a solvent which is inert toward the reactants under the reaction conditions. Examples of possible distributing agents or solvents are nitriles, such as acetonitrile, ethers, such as diethyl ether, tetrahydrofuran and dioxane, alcohols, such as methanol, ethanol, propanol or isopropanol, and water. In a preferred embodiment, the amine of the formula II is reacted with the carboxylic acid chloride in question, of the formula III, advantageously in the presence of an acid-binding agent, such as potassium carbonate or sodium carbonate, an alkali metal or alkaline earth metal hydroxide or alcoholate or an organic base, such as triethylamine, pyridine, picoline, or quinoline, or in the presence of an excess of the amine of the formula (II) employed, in general at temperatures from 0° to 120° C., preferably from 20° to 60° C. The reaction times can be from a few minutes up to 2 hours.

If the reaction is carried out in organic solvents, the products of the formula I are advantageously isolated by filtering off the precipitate of the salts formed as by-products, and subsequently concentrating the filtrates. The products can advantageously be isolated from aqueous reaction mixtures by extraction with a polar organic solvent, such as methylene chloride, chloroform or trichloroethylene, and evaporation of the extracts. The products can then be purified by distillation or recrystallization from an organic, preferably moderately polar solvent, such as toluene, dimethylbenzene, benzene, cyclohexane, methanol, ethanol, diethyl ether or diisopropyl ether, or non-polar solvents, such as petroleum ether, or a mixture of such solvents.

The 4-isoxazolecarboxylic acid derivatives of the formula III can be prepared from the corresponding carboxylic acids by customary methods. The 4-isoxazolecarboxylic acids required as starting substances for this (formula III: X=OH) are known (German Pat. No. 634,286, European Patent Application No. 12,435 and Gazz. Chim. Ital. 96 (4), 443–453 (1966)) or can be prepared analogously.

Another process for the preparation of compounds of the formula I comprises reacting a 2-acylacetic acid amide of the formula IV

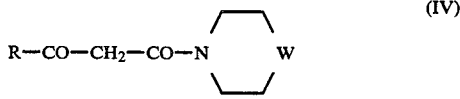

(IV)

with an ether of ortho-formic acid of the formula HC(OR$^1$)$_3$ (V), in which R$^1$ is alkyl having from 1 to 4 carbon atoms, and cyclizing the resulting 2-alkoxymethylene-2-acyl acetic acid amide of the formula VI

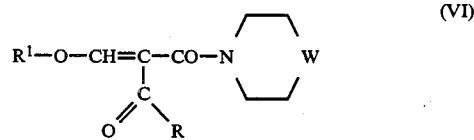

(VI)

with hydroxyl amine to yield a product of formula I.

A procedure can be followed here, for example, in which the amide of the formula IV is warmed with advantageously at least an equimolar amount of an orthoformic acid ester of the formula V, if appropriate in the presence of an alcohol-binding agent, to a temperature of 80° to 150° C., preferably to the boiling point of the mixture, and the 2-alkoxymethylene-2-acylacetic acid amide of the formula VI thus obtained is isolated and then reacted with advantageously at least an equimolar amount of hydroxylamine in an organic solvent or solvent mixture, preferably in a water-miscible cyclic ether, such as tetrahydrofuran or dioxane, if appropriate with the addition of up to 2 parts by volume, preferably up to 1 part by volume, of water per part by volume of organic solvent, in general at a temperature from 0° to 130° C., preferably from 20° to 100° C. The reaction times are usually between a few minutes and about 5 hours.

Another convenient method for the preparation of the isoxazoles of the formula I comprises reacting the 2-acylacetic acid amides of the formula IV with secondary amines of the formula HNR$^2$R$^3$ (VII) in which R$^2$ and R$^3$ represent identical or different alkyl radicals with 1 to 4 carbon atoms or, together with the N atom, to which they are bonded, represent a ring, such as pyrrolidine, piperidine or morpholine, to give the enamine of the formula VIII

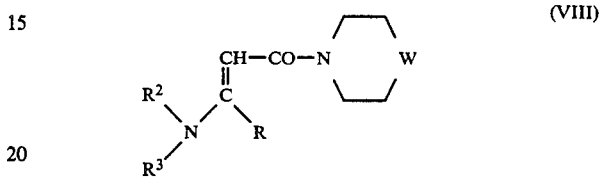

(VIII)

and cyclizing these products, advantageously in the presence of dehydrating agents, with the nitrile oxide intermediately produced from nitromethane.

The enamines VIII required as intermediates can be synthesized by reacting the acylacetic acid amide of the formula IV with advantageously at least an equimolar amount of the secondary amine of the formula VII, advantageously with the addition of a catalytic amount of acid, such as formic acid or p-toluenesulfonic acid, advantageously in a distributing agent or solvent which is inert toward the reactants under the reaction conditions, for example an aromatic hydrocarbon, such as toluene, in general at temperatures from 60° to 160° C., preferably 80° to 130° C.

The subsequent cyclization reaction of the enamine of the formula VIII with nitromethane to give the product of the formula I is effected in the customary manner (G. Stork et al., J. Amer. Chem. Soc. 89, 1967, pages 5461–5462), by reaction either in the presence of an isocyanate, such as phenyl isocyanate, and an organic base, such as, for example, triethylamine, in a hydrocarbon, for example benzene or toluene, at temperatures from 0° C. to the boiling point of the reaction mixture, or under the influence of an inorganic acid halide, for example phosphorus oxychloride, in a halogenated hydrocarbon, such as, for example, chloroform, the reaction preferably being carried out at about 0° C.

Due to their pharmacological properties, the isoxazole compounds of the formula I according to the invention can be used as medicaments, in particular as analgesics and antipyretics. They can be administered either by themselves, if appropriate in the form of microcapsules, or as mixtures with suitable excipients.

The invention thus also relates to medicaments which consists of a compound of the formula I or contain this active compound in addition to a pharmaceutically usual and physiologically acceptable excipient, diluent and/or other auxiliaries. These agents can be administered orally, rectally or parenterally, oral and rectal administration being preferred.

Examples of suitable solid or liquid pharmaceutical formulations are granules, powders, coated tablets, tablets, capsules, suppositories, syrups, juices suspensions, emulsions, drops or injectable solutions, and products with protracted release of the active compound. Examples which may be mentioned of excipients which are frequently used are calcium carbonate, calcium phosphates, various sugars or types of starch, cellulose derivatives, gelatine, vegetable oils, polyethylene glycols and physiologically acceptable solvents.

The compounds according to the formula I can also be used in combination with other suitable active compounds, for example other analgesics which have an action on the central nervous system, such as codeine, stimulants which act on the central nervous system, such as caffeine, or other spasmolytics.

The products are preferably prepared and administered in dosage units, each unit containing a particular dose of active substance according to the formula I. In the case of solid dosage units, such as tablets, capsules and suppositories, this dose can be up to 1,500 mg, preferably 100 to 600 mg, and in the case of injection solutions in ampoule form, it can be up to 1,000 mg, perferably 50 to 500 mg.

For the treatment of an adult patient suffering from pain and/or fever, daily doses of 200 to 3,000 mg of active compound, preferably 500 to 1,000 mg, in the case of oral or rectal administration, and 100 to 1500 mg, preferably 200 to 600 mg, in the case of intravenous administration, are administered depending on the activity of the compound according to the formula I on humans. For children, for example, as little as one-fifth of the above-mentioned low values may be adequate as the daily dose, depending on their age.

Under certain circumstances, however, higher or lower daily doses may also be appropriate. The daily dose can be administered either by a single administration in the form of an individual dosage unit or more smaller dosage units, or by multiple administration of subdivided doses at certain intervals of time.

PREPARATION EXAMPLES

The structure of all the compounds described below was confirmed by elemental analysis and the IR and $^1$H-NMR spectra.

(1) N-(5-Methyl-4-isoxazolylcarbonyl)-piperidine (a) A solution of 0.4 mol (34.1 g) of piperidine in 50 ml acetonitrile is added dropwise to 0.2 mol (29.1 g) in 5-methyl-4-isoxazolecarboxylic acid chloride, dissolved in 350 ml of acetonitrile, at room temperature with stirring such that the temperature of the reaction solution does not rise above 40° C. Stirring is then continued for 15 minutes and the mixture is subsequently cooled to room temperature. The piperidine hydrochloride precipitated is filtered off with suction and the filtrate is concentrated under reduced pressure. The oily residue is dissolved in 300 ml of methylene chloride and the solution is washed with 40 ml of 2N sodium hydroxide solution.

The methylene chloride phase is separated off and the aqueous phase is extracted again with 200 ml of methylene chloride. The combined methylene chloride phases are shaken with 70 ml of 0.2N hydrochloric acid, washed neutral with water and, after drying over sodium sulfate, dried under reduced pressure. The oily residue is distilled under reduced pressure. N-(5-Methyl-4-isoxazolylcarbonyl)-piperidine is thus obtained with a boiling point of 102° to 112° C. under 4 to 7 mbar (bulb tube distillation), which solidifies after a short time: Melting point (from methylcyclohexane) 40° to 43° C.

(b) 0.4 mol (34.1 g) of piperidine and 40 ml of 10N sodium hydroxide solution are added dropwise to 0.4 mol (58.2 g) of 5-methyl-4-isoxazolecarboxylic acid chloride, emulsified in 300 ml of water, such that the temperature of the reaction mixture does not rise above 35° C. 40 ml of 2N sodium hydroxide solution are then added and the mixture is extracted with 300 ml methylene chloride. The aqueous phase is extracted once more by shaking with 200 ml of methylene chloride. The combined methylene chloride phases are washed with water and, after drying over sodium sulfate, evaporated to dryness under reduced pressure. N-(5-Methyl-4-isoxazolylcarbonyl)-piperidine is thus obtained, the product having, after recrystallization from methylcyclohexane, a melting point of 40° to 43° C.

(2) N-(5-Ethyl-4-isoxazolylcarbonyl)-piperidine 0.2 mol (17.0 g) of piperidine is added dropwise to 0.1 mol (16.0 g) of 5-ethyl-4-isoxazolecarboxylic acid chloride dissolved in 200 ml of acetonitrile, at room temperature with stirring. Stirring is continued for 20 minutes and the mixture is then cooled to room temperature and the piperidine hydrochloride precipitated is filtered off with suction. The filtrate is concentrated under reduced pressure. An oily residue is obtained, and is taken up in 200 ml of methylene chloride, and the mixture is washed first with 100 ml of 2N hydrochloric acid and then with water. After drying over sodium sulfate, the mixture is concentrated under reduced pressure and the oily residue is distilled under reduced pressure (bulb tube distillation). N-(5-Ethyl-4-isoxazolylcarbonyl)-piperidine of boiling point (7 mbar) 90°–110° C. is thus obtained.

(3) N-(5-Methyl-4-isoxazolylcarbonyl)-pyrrolidine 0.3 mol (21.3 g) of pyrrolidine is added dropwise to 0.15 mol (21.8 g) of 5-methyl-4-isoxazolecarboxylic acid chloride, dissolved in 50 ml of acetonitrile, with stirring, such that the temperature of the reaction solution does not rise above 30° C.

After subsequently stirring at room temperature for 1.5 hours, the reaction solution is concentrated under reduced pressure, the oily residue is dissolved in 200 ml of methylene chloride and the solution is shaken with 30 ml of 0.1N hydrochloric acid. After the organic phase has been washed with water, it is dried over sodium sulfate and evaporated to dryness under reduced pressure.

N-(5-Methyl-4-isoxazolylcarbonyl)-pyrrolidine is thus obtained; the product can be recrystallized from petroleum ether and has a melting point of 51° to 53° C.

The following compounds of the formula I are prepared analogously to the examples described above:

(4)

4-Methyl-1-(5-methyl-4-isoxazolylcarbonyl)-piperidine of melting point 44° to 45° C., prepared from 5-methyl-4-isoxazolecarboxylic acid chloride and 4-methyl-piperidine.

(5) N-(5-Methyl-4-isoxazolylcarbonyl)-thiomorpholine of melting point 64.5° to 65° C., prepared from 5-methyl-4-isoxazolecarboxylic acid chloride and thiomorpholine.

(6)
4-Hydroxy-1-(5-methyl-4-isoxazolylcarbonyl)-piperidine of melting point 70.5° to 72.5° C., prepared from 5-methyl-4-isoxazolecarboxylic acid chloride and 4-hydroxypiperidine.

(7) N-(4-Isoxazolylcarbonyl)-piperidine of melting point 78° to 81° C., prepared from 4-isoxazolecarboxylic acid chloride and piperidine.

(8)
N-(5-Trifluoromethyl-4-isoxazolylcarbonyl)-piperidine of boiling point (4 mbar) 62° to 68° C., prepared from 5-trifluoromethyl-4-isoxazolecarboxylic acid chloride and piperidine.

(9) N-(5-Propyl-4-isoxazolylcarbonyl)-piperidine of boiling point (4 mbar) 84° to 92° C., prepared from 5-propyl-4-isoxazolecarboxylic acid chloride and piperidine.

(10) N-(5-Methyl-4-isoxazolylcarbonyl)-morpholine of melting point 42° to 44° C., prepared from 5-methyl-4-isoxazolecarboxylic acid chloride and morpholine.

PHARMACOLOGICAL TESTING AND RESULTS

1. Analgesic action (a) Acetic acid extension test on mice in accordance with the method of R. Koster et al., Fed. Prod. 18, 412 (1959)

Female mice of a N.M.R.I. strain with a body weight (BW) of between 21 and 28 g were used as the experimental animals. Groups of in each case 12 animals received 0.1 ml/10 g BW of a 0.6% strength acetic acid solution, injected intraperitoneally. The test substances were administered 30 minutes beforehand. Immediately after the acetic acid injection, the animals were placed individually and the typical extension movements occurring within 15 minutes were counted, these consisting of brief flexing of the abdominal muscles with withdrawal of the sides and subsequent extension of the rear of the body and of at least one rear extremity.

To evaluate the analgesic effect, the number of extension reactions was related to those of an untreated control group, those animals which showed fewer than half of the average extension movements performed by the control animals being evaluated as showing an analgesic effect.

The test substances were administered orally in a volume of 10 ml/kg BW in 1% strength aqueous carboxymethylcellulose (CMC) suspension.

(b) Modified Randall-Selitto hyperalgesia test on rats in accordance with the method of Atkinson et al., J. Pharm. Pharmac. 26, 727 (1974)

Male Sprague-Dawley rats with a body weight of 200 to 300 g were used as the experimental animals. The experimental animals were given a subplantar injection of 0.2 ml of brewer's yeast suspension (40% of yeast in 0.9% strength NaCl solution) into the left hind paw under mild ether anaesthesia. After 5 hours, the gait of the animals over a metal grating was evaluated according to the following scale:

0 = three-legged gait
0.5 = severe limping
1 = normal gait

The evaluation was effected by determining the percentage of animals evaluated with stage 1 or 0.5, two animals given 0.5 being regarded as showing an analgesic effect.

The test substances were administered orally, to animals which had been fasted for 15 hours, in CMC suspension in a volume of 10 ml/kg BW two hours before the evaluation of the animals. In order to exclude subjective influences, the evaluation was performed by two people independently of one another and without knowledge of the pretreatment of the animals (n = 10/dose). The $ED_{50}$ values were determined with the aid of linear regression in accordance with the method of Fieller and Sidak.

2. Antipyretic action

The investigations were carried out on female Sprague-Dawley rats with a body weight of 150 g and fed on drinking water ad libitum and a standard diet. The increased body temperature was induced by subcutaneous injection of 10 ml/kg of 15% strength (weight-/volume) brewer's yeast suspension in 0.9% strength NaCl solution, after which the food was withdrawn from the animals until the end of the experiment. 18 hours after the yeast injection, the test substances were administered orally in CMC suspension in a volume of 10 ml/kg BW. The body temperature was measured rectally by means of second thermometers at room temperature (24° C.). The number of animals was n = 6 per dose. The average reduction in body temperature in comparison with the simultaneous value of the untreated control animals was recorded.

3. Gastrointestinal ulcerogenicity

In this test on male Sprague-Dawley rats with a body weight of between 200 and 300 g, an increased sensitivity of the gastric mucosa toward the ulcerogenic action of non-steroid antiflammatories was induced by hunger stress (withdrawal of food for a total of 72 hours).

48 hours before administration of the test substances, the food was withdrawn from the animals until the end of the experiment, the animals having free access to drinking water.

24 hours after oral administration of the product, the animals were sacrificed and the stomachs were removed, cut along the lesser curvature, cleaned under running water and inspected for lesions in the mucous membrane. All the macroscopically visible lesions of the mucosa in the glandular atomach were regarded as ulcers. The proportion of animals with ulcers per dose was determined.

The test substances were administered as a solution in CMC suspension in a volume of 1 ml/100 g of body weight. The $UD_{50}$ (dose at which 50% of the animals had ulcers) was determined with the aid of Probit analysis and the confidence range was determined by the method of Fieller.

4. Acute toxicity

The $LD_{50}$ values were determined after oral administration of the test products to male and female Wistar rats with a body weight of 130–150 g in accordance with the method of Litchfield and Wilcoxon. The animals were used in the experiment after being fasted for about 18 hours and only received food again five hours after administration of the product. After a three-week observation period, they were sacrificed with chloroform and autopsied. The organs were assessed macroscopically. The test compounds were dissolved in 1% strength CMC suspension and administered to the rats through a stomach tube in a volume of 5 ml/kg BW.

5. Results

In the extension test on mice, the compounds of the formula I according to the invention display a powerful analgesic activity, the degree of which is superior to or approximately equivalent to that of the two standard analgesics Paracetamol and acetylsalicylic acid (Table 1). Acetylsalicylic acid was additionally used as a comparison substance in view of its general importance as an analgesic, although it differs from the compounds according to the invention—as described above—in its action mechanism as an inhibitor of peripheral prostaglandin biosynthesis and hence as an antiinflammatory analgesic. The two isoxazole compounds known from German Pat. No. 634,286, with an inhibition of 25%, are within the range of scatter of the method and are thus analgesically inactive.

TABLE 1

| Analgesic action in the acetic acid extension test on mice | |
|---|---|
| Compound of example | Animals which showed analgesic effect in % after an oral dose of 158 mg/kg |
| 1 | 83 |
| 2 | 83 |
| 3 | 83 |
| 4 | 67 |
| 5 | 59 |
| 6 | 50 |
| 7 | 50 |
| 8 | 75 |
| 9 | 67 |
| 10 | 42 |
| 3,5-Dimethyl-4-isoxazole-carboxylic acid piperidide* | 25 |
| 5-Methyl-4-isoxazolecarboxylic acid N,N—diethylamide** | 25 |
| Paracetamol | 50 |
| Acetylsalicylic acid | 48 |

*German Patent 634,286, Example 6
**German Patent 634,286, Example 5 (no allocation of the methyl group there)

The superiority of the compounds according to the invention over the standard products could also be clearly demonstrated in the other test models (Table 2). Thus, for example, the compound of Example 1 displays a clearly more advantageous average effective doses ($ED_{50}$) in the specific pain model according to Randall-Selitto. At 85 mg/kg, it is twice as active as acetylsalicylic acid and four times as powerful than Paracetamol. In the pain test on mice, its effectiveness is at least three times that of the two comparison products, with an $ED_{50}$ of 45 mg/kg on oral administration.

Their therapeutic range resulting from the relation to the toxicity ($LD_{50}:ED_{50}$) in the two pain tests is also about two and three times as favorable as that of the two comparison products.

To evaluate the therapeutic acceptability of analgesics, the gastric ulcerogenicity is also particularly decisive. The compound of Example 1, for example, shows an outstanding tolerance here, since no lesions of the mucous membrane were detected in doses of up to 400 mg/kg. Acetylsalicylic acid has an average ulcerogenic dose ($UD_{50}$) of 31 mg/kg and thus reflects the side effect which is also most frequent in the case of use on humans.

As already mentioned above, the compounds of the formula I according to the invention also have powerful antipyretic properties. In the yeast fever test on rats (Table 3), for example, the compound of Example 1 shows a reduction in fever with an oral dose of 50 mg/kg which is both more powerful and clearly lasts longer than that of the comparison product Paracetamol with twice the dose of 100 mg/kg, administered orally.

TABLE 2

| | Analgesic action, toxicity, ulcerogenicity and therapeutic range | | | | | |
|---|---|---|---|---|---|---|
| | Analgesic action $ED_{50}$ in mg/kg, administered orally | | Toxicity $LD_{50}$ in mg/kg | Ulcerogenicity $UD_{50}$ in mg/kg | Therapeutic range $LD_{50}:ED_{50}$ | |
| Test substance | Randall-Selitto test (Rat) | Acetic acid extension test (Mouse) | administered orally (Rat) | administered orally (Rat) | Randall-Selitto test | Acetic acid extension test |
| Acetylsalicylic acid | 182 | 138 | 1,500 | 31 | 8.2 | 10.9 |
| Paracetamol | 334 | 155 | 1,944 | >400 | 5.8 | 12.5 |
| Example 1 | 85 | 45 | 1,240 | >400 | 14.6 | 27.6 |

TABLE 3

| | Antipyretic action in rats | | | | |
|---|---|---|---|---|---|
| Test substance | Dose in mg/kg Administered orally | Reduction in body temperature in °C. at time t (in minutes) | | | |
| | | 60 | 120 | 180 | 240 min. |
| Paracetamol | 100 | 1.3 | 1.1 | 0.4 | 0 |
| Example 1 | 50 | 1.3 | 1.6 | 1.3 | 0.8 |
| Example 1 | 100 | 2.0 | 2.0 | 1.5 | 1.1 |

It is known from the literature that Paracetamol is unsuitable for treating pain of spastic origin in the biliary, gastrointestinal and urogenital tract because of the absence of a spasmolytic action component (R. K. Liedtke, Medizinische Klinik 77 (1982), pages 34–40). In accordance with this, Paracetamol exhibits no inhibiting effect on spasms induced, for example, with potassium chloride, on the isolated pig ureter. In contrast, the compounds of the formula I exert a significant inhibiting action in this experimental design. Thus, for example, the $ED_{50}$ value for the compound of Example 1 is a concentration of 410 µg/ml.

The compounds according to the invention consequently have the great advantage over Paracetamol that they can also be used for the therapy of pain of spastic origin.

Finally, another advantage is the water-solubility of the compounds according to the invention, which makes possible the preparation of formulations which can be administered parenterally.

We claim:
1. A compound of the formula I,

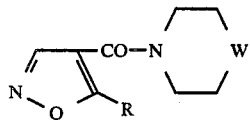

(I)

in which
R represents hydrogen, alkyl having up to 4 carbon atoms or haloalkyl having up to 2 carbon atoms and W represents a direct bond, $CH_2$, $CH-CH_3$, $CH-C_2H_5$, CHOH, O or S.

2. A compound as claimed in claim 1, wherein R is a methyl, ethyl or trifluoromethyl group.

3. A compound as claimed in claim 2, wherein W is $CH_2$.

4. A compound as claimed in claim 1, wherein R is a methyl group and W is $CH_2$.

5. A pharmaceutical composition for use in the treatment of pains or fever or both, containing an effective amount of a compound of the formula I as claimed in claim 1.

6. A pharmaceutical composition for use in the treatment of pains or fever or both, containing an effective amount of a compound of the formula I as claimed in claim 4.

7. A pharmaceutical composition for use in the treatment of pains or fever or both, being in the form of solid dosage units, each dose containing from 100 to 600 mg of the active ingredient of a compound as claimed in claim 1.

8. A pharmaceutical composition for use in the treatment of pains or fever or both, being in the form of ampoules, each ampoule containing from 50 to 500 mg of the active ingredient of a compound as claimed in claim 1.

9. A method for treating a patient suffering from pains or fever which comprises administering to said patient a pharmaceutical composition as claimed in claim 5.

* * * * *